US012655169B2

(12) United States Patent
Shi et al.

(10) Patent No.: US 12,655,169 B2
(45) Date of Patent: Jun. 16, 2026

(54) ARABINOSE AND PREPARATION AND USE THEREOF

(71) Applicant: THOMSON BIOTECH (XIAMEN) PTE. LTD., Xiamen (CN)

(72) Inventors: Guoliang Shi, Xiamen (CN); Weijun Lin, Xiamen (CN); Xubin Cai, Xiamen (CN); Yujuan Wang, Xiamen (CN); Yongcheng Xiao, Xiamen (CN); Shunzhi Xiao, Xiamen (CN)

(73) Assignee: THOMSON BIOTECH (XIAMEN) PTE. LTD., Xiamen (CN)

( * ) Notice: Subject to any disclaimer, the term of this patent is extended or adjusted under 35 U.S.C. 154(b) by 735 days.

(21) Appl. No.: 17/998,902

(22) PCT Filed: Mar. 25, 2022

(86) PCT No.: PCT/CN2022/083083
§ 371 (c)(1),
(2) Date: Nov. 15, 2022

(87) PCT Pub. No.: WO2023/130594
PCT Pub. Date: Jul. 13, 2023

(65) Prior Publication Data
US 2023/0406876 A1     Dec. 21, 2023

(30) Foreign Application Priority Data

Jan. 6, 2022    (CN) .......................... 202210010286.6
Jan. 27, 2022   (CN) .......................... 202210101531.4

(51) Int. Cl.
| | |
|---|---|
| *C07H 3/02* | (2006.01) |
| *A61K 9/16* | (2006.01) |
| *A61P 1/00* | (2006.01) |

(52) U.S. Cl.
CPC ................. *C07H 3/02* (2013.01); *A61K 9/16* (2013.01); *A61P 1/00* (2018.01)

(58) Field of Classification Search
CPC ............... C07H 3/02; A61P 1/00; A61K 9/16
USPC ........................................................... 514/23
See application file for complete search history.

(56) References Cited

U.S. PATENT DOCUMENTS

| | | | |
|---|---|---|---|
| 2016/0213702 A1 | 7/2016 | Von Maltzahn et al. | |
| 2019/0248824 A1* | 8/2019 | Chassagne | .............. F26B 21/14 |

FOREIGN PATENT DOCUMENTS

| | | | |
|---|---|---|---|
| CN | 101475972 | * | 7/2009 |
| CN | 101665524 A | | 3/2010 |
| CN | 102659854 | * | 9/2012 |
| CN | 104892688 | * | 9/2015 |
| CN | 104892688 A | | 9/2015 |
| CN | 111202244 A | | 5/2020 |
| CN | 111544436 A | * | 8/2020 |
| EP | 1167536 A1 | | 1/2002 |
| JP | 2001286294 A | | 10/2001 |
| JP | 2004510163 A | | 4/2004 |
| JP | 2004261039 A | | 9/2004 |
| JP | 2009207462 A | | 9/2009 |

OTHER PUBLICATIONS

Tyson et al. Crystallization Behavior and Crystallographic Properties of DL-Arabinose and DL-Xylose Diastereomer Sugars. Cryst. Growth Des. 2022, 22, 1371-1383 (Published: Jan. 12, 2022) (Year: 2022).*
Hu, Biao, "Study on the Crystallization Kinetics Process and Mechanisms of L-Arabinose", Chinese Doctoral Dissertations Fulltext Database, Jun. 1, 2015, pp. 1-9.

* cited by examiner

*Primary Examiner* — Yih-Horng Shiao
(74) *Attorney, Agent, or Firm* — NKL Law; Allen Xue

(57) ABSTRACT

An L-arabinose is prepared through the following processes: (1) dissolving L-arabinose starting material in water, adding activated carbon, filtering, and removing the activated carbon to give a clear filtered sugar liquid; and (2) subjecting 40-55% (v %) of the clear filtered sugar liquid obtained in step (1) to evaporation until sugar degree reaches 55-65% Brix, adding the remaining clear filtered sugar liquid in a fed-batch manner after adding a proper amount of the L-arabinose starting material as seed crystal, and continuing concentration after the fed-batch addition is completed. The process of preparing the arabinose and the preparation thereof does not involve addition of any auxiliary material nor complicated granulation processes. The obtain product can be directly applied as a bowel cleanser drug. The range of particle size is controllable.

8 Claims, 4 Drawing Sheets

| Index | Angle | d Value | Net Intensity | Gross Intensity | Rel. Intensity |
|---|---|---|---|---|---|
| 1 | 9.160 ° | 9.64720 A | 1113.30 | 1297.18 | 2.2% |
| 2 | 14.416 ° | 6.13962 A | 50432.4 | 50641.2 | 100.0% |
| 3 | 15.100 ° | 5.86278 A | 40.1198 | 245.063 | 0.1% |
| 4 | 16.450 ° | 5.38433 A | 20280.9 | 20489.3 | 40.2% |
| 5 | 18.292 ° | 4.84580 A | 4084.54 | 4372.04 | 8.1% |
| 6 | 18.940 ° | 4.68165 A | 1493.37 | 1678.99 | 3.0% |
| 7 | 20.556 ° | 4.31726 A | 25541.1 | 25753.0 | 50.6% |
| 8 | 22.655 ° | 3.92183 A | 161.267 | 375.923 | 0.3% |
| 9 | 22.943 ° | 3.87321 A | 7418.31 | 7639.67 | 14.7% |
| 10 | 23.404 ° | 3.79789 A | 1963.57 | 2184.14 | 3.9% |
| 11 | 24.734 ° | 3.59863 A | 1601.76 | 2135.88 | 3.8% |
| 12 | 26.012 ° | 3.42269 A | 922.030 | 1133.64 | 1.8% |
| 13 | 26.743 ° | 3.33081 A | 634.586 | 980.518 | 1.3% |
| 14 | 27.443 ° | 3.24799 A | 17848.8 | 18166.2 | 35.4% |
| 15 | 27.638 ° | 3.20395 A | 39004.9 | 39239.7 | 77.3% |
| 16 | 28.854 ° | 3.08127 A | 5655.29 | 5967.18 | 11.2% |
| 17 | 29.487 ° | 3.02677 A | 2454.02 | 2776.41 | 4.9% |
| 18 | 30.829 ° | 2.89601 A | 486.298 | 796.660 | 1.0% |
| 19 | 32.811 ° | 2.74366 A | 486.386 | 805.834 | 0.9% |
| 20 | 33.181 ° | 2.69934 A | 15577.4 | 15939.1 | 30.9% |
| 21 | 33.490 ° | 2.67360 A | 1096.16 | 1463.51 | 2.2% |
| 22 | 34.467 ° | 2.60002 A | 1304.37 | 1667.50 | 2.6% |
| 23 | 35.155 ° | 2.55088 A | 3074.79 | 3422.82 | 6.1% |
| 24 | 36.010 ° | 2.49204 A | 2261.83 | 2574.99 | 4.5% |
| 25 | 37.188 ° | 2.41582 A | 750.303 | 1041.30 | 1.5% |
| 26 | 38.113 ° | 2.35928 A | 453.807 | 752.856 | 0.9% |
| 27 | 38.342 ° | 2.34572 A | 376.489 | 676.580 | 0.7% |
| 28 | 39.209 ° | 2.29680 A | 759.731 | 1137.22 | 1.5% |
| 29 | 39.621 ° | 2.27390 A | 794.398 | 1557.18 | 1.6% |

FIG. 1 Continued

Sample name: TCSB20210328-2
Temperature: 23 °C   humidity: 54%
Instrument model: PE Spectrum Two

ARABINOSE AND PREPARATION AND USE THEREOF

CROSS-REFERENCE TO RELATED APPLICATIONS

This application is a U.S. national entry of PCT International Application No. PCT/CN2022/083083, filed on Mar. 25, 2022, which claims priority to the Patent Application with the application No. 202210010286.6 and entitled "L-ARABINOSE AND PREPARATION METHOD THEREFOR AND USE THEREOF" filed with China National Intellectual Property Administration on Jan. 6, 2022, and the Patent Application with the application No. 202210101531.4 and entitled "ARABINOSE GRANULES AND PREPARATION METHOD THEREFOR AND USE THEREOF" filed with China National Intellectual Property Administration on Jan. 27, 2022, the content of each is incorporated herein by reference in its entirety.

TECHNICAL FIELD

The present disclosure relates to the field of pharmaceutical chemical engineering, and particularly to an arabinose and a preparation and use thereof.

BACKGROUND

As the endoscopy technology has developed, enteroscopy has been widely applied in clinical practice and has become one of the primary means of diagnosing and treating various intestinal diseases. Enteroscopy is largely affected by bowel preparation. It is extremely important to perform adequate bowel preparation to improve the quality of colonoscopic images and thus to increase the detection rate of colonic diseases.

Further, in the conventional bowel cleansing process, magnesium sulfate and PEG and the like are unacceptable to many people for their textures, which, coupled with the large oral dosage, make it difficult for patients to take them. Therefore, the correct dosage is not properly taken in accordance with medical advice. The reduced compliance is an important factor that contributes to incomplete bowel cleansing.

L-Arabinose ($C_5H_{10}O_5$), also known as L(+)-arabinose, is an aldopentose. It is a monosaccharide originally isolated from gum arabic. Free L-arabinose is rarely found in nature. It usually binds to other monosaccharides and is present in heteropolysaccharide form in colloids, hemicelluloses, bacterial polysaccharides and some glycosides. Free L-arabinose has ever been found only in the core material of trees of the families Pinaceae and Cupressaceae. L-arabinose is more and more extensively applied in food, pharmaceuticals and other areas. Research shows that L-arabinose has the effect of assisting in reducing blood sugars and losing weight and has the good function of moistening and emptying the bowels. However, studies on the development of medicinal products of L-arabinose and on its manufacturing processes that are beneficial to medicinal safety and large-scale production in the prior art are still limited.

A Chinese patent with publication No. CN102146102A discloses extraction of L-arabinose from the starting material gum arabic. After acid-catalyzed hydrolysis, alkaline neutralization and concentration, extraction is performed with ketones, alcohols and ethers. The process involves use of large amounts of organic solvents, which seriously pollute the environment.

A Chinese patent with publication No. CN1373135A discloses a method of extracting arabinose from gum arabic using a two-column method. In the method, after hydrolysis with inorganic acids, alkaline neutralization and extraction with alcohols, the resulting mixture of rhamnose and arabinose is separated through columns with large amounts of organic solvents such as n-butanol, ethyl acetate, isopropanol and acetic acid and the like as column developing agents. The purity is up to 99.5%; however, the process is complicated, and the organic solvents readily pollute the environment. The process is not environment-friendly.

A Chinese patent with publication No. CN104744525A discloses a method of extracting arabinose from gum arabic. The starting material is subjected to hydrolysis, alkaline neutralization, adsorptive decolorization, desalting by electrodialysis, removal of impurities by adsorptive separation, and crystallization. The purity is up to 98%. The above process is relatively environment-friendly. However, the crystallization process also involves use of organic solvents such as methanol/ethanol and the like for hot dissolution, and powdered L-arabinose is obtained only after up to 24-72 h of cooling and crystallization.

L-arabinose products hold relatively great promise of being applied to bowel cleansers. However, there is a series of problems with further developing L-arabinose into medicinal preparations. For example, arabinose needs to be combined with other auxiliary materials for ease of administration, which leads to an increase in the safety risk due to the increased introduction of impurities when large doses of preparation are taken. For example, it is hard to obtain preparations that are up to the standards of quality specified in the pharmacopoeia; or the process is not suitable for industrial production as it is complicated and costly.

Granules are dry granulated preparations with certain granularity prepared by mixing the starting material drug with suitable auxiliary materials. The granularity range specified in the *Chinese pharmacopoeia* (2020) is that coarse particles cannot pass through a No. 1 sieve (10 mesh, 2000 μm) and that the total quantity of coarse particles which can pass through a No. 5 sieve (80 mesh, pore size of 180 μm) should not exceed 15%.

A Chinese patent application with publication No. CN111202244A discloses a granulated arabinose, which is prepared by using arabinose solution as an adhesive instead of adding additional adhesives so that powdered arabinose is granulated in the presence of the adhesive. However, the quantities of the part of the obtained arabinose granules that can pass through a 80 mesh sieve vary between 38% and 78%, which does not meet the general requirements for granules in the pharmacopeia. Moreover, in the application, the obtained granulated arabinose still needs to be combined and mixed with other auxiliary materials such as sweeteners and the like to further prepare granules and capsules.

Therefore, researchers need to study the properties, the preparation process and the preparation performance of L-arabinose so as to obtain L-arabinose products that can effectively improve patient compliance in the bowel cleansing process and thus the quality of bowel preparation, and further to obtain preparations that are up to the pharmaceutical standards of quality, as well as to develop a preparation process that is beneficial to industrialization and is safe, environment-friendly and feasible.

SUMMARY

In order to solve the problems in the prior art, in a first aspect, the present disclosure provides an L-arabinose, which is β-L-(+)-arabinose.

According to an embodiment of the present disclosure, the L-arabinose has the crystal structure (monocrystal) described below:

the crystal structure is an orthorhombic crystal system, having a $P2_12_12_1$ space group and the following unit cell parameters:

a=4.78120(10)Å,
b=6.43740(10)Å,
c=19.50095(3)Å,
$\alpha=90°$, $\beta=90°$, $\gamma=90°$, V=600.208(18)Å$^3$, Z=4, F(000) =320.0.

According to an embodiment of the present disclosure, a crystal of the L-arabinose is characterized by X-ray powder diffraction peaks measured using Cu-Kα radiation at 20 angles of 14.416±0.20°, 16.450±0.20°, 20.556±0.20°, 27.443±0.20°, 27.828±0.20° and 33.161±0.20°. Preferably, a crystal of the L-arabinose is characterized by X-ray powder diffraction peaks measured using Cu-Kα radiation at 20 angles of 14.416±0.20°, 16.450±0.20°, 20.556±0.20°, 22.943±0.20°, 27.443±0.20°, 27.828±0.20° and 33.161±0.20°.

According to an embodiment of the present disclosure, the crystal has an X-ray powder diffraction pattern substantially as shown in FIG. 1.

According to an embodiment of the present disclosure, the crystal has an infrared spectrum substantially as shown in FIG. 2.

According to an embodiment of the present disclosure, the L-arabinose has an average particle size ranging from 100 μm to 600 μm, preferably from 100 μm to 300 μm, e.g., 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm or 290 μm.

According to an embodiment of the present disclosure, the L-arabinose comprises≤0.04% galactose; preferably, the L-arabinose comprises≤0.01% galactose; more preferably, the L-arabinose comprises 0.005% galactose.

According to an embodiment of the present disclosure, the L-arabinose comprises≤0.05% fructose; more preferably, the L-arabinose is free of fructose (i.e., fructose content=0%).

In a second aspect, the present disclosure also provides a preparation method for the L-arabinose.

In some embodiments, the preparation method uses scheme 1, which comprises the following steps:

(1) dissolving L-arabinose starting material in water, adding activated carbon, filtering, and removing the activated carbon to give a clear filtered sugar liquid; and (2) adding about half of the clear filtered sugar liquid obtained in step (1) to an evaporative crystallization tank, evaporating the sugar liquid until sugar degree reaches 55-65% Brix, adding the remaining half of the clear filtered sugar liquid in a fed-batch manner after adding a proper amount of the L-arabinose starting material as seed crystal, and continuing concentration after the fed-batch addition is completed.

According to an embodiment of the present disclosure, the L-arabinose starting material is used as seed crystal after being ground, sieved and homogenized. It can be understood by those skilled in the art that conventional industrial sieves (40-200 mesh) or pharmacopeia standard sieves (No. 3, No. 4, No. 5, No. 6, No. 7, No. 8 and No. 9) can be used; for example, No. 5 and No. 6 pharmacopeia standard sieves are used. In some embodiments, L-arabinose starting material is ground and sieved with No. 5 and No. 6 pharmacopeia standard sieves, and the part that can pass through the No. 5 sieve but not through the No. 6 sieve is kept.

According to an embodiment of the present disclosure, in step (1) of the scheme 1, the starting material and the water are in a ratio by mass of 1:(0.5-3), preferably 1:(1-1.5), e.g., 1:1.1, or 1:1.2; the starting material and the activated carbon are in a ratio by mass of 1:(0.0005-0.01), preferably 1:(0.0005-0.0015), e.g., 1:0.0005, or 1:0.001; In step (2), the fed-batch addition is performed for a time period of 6-24 h, e.g., 9 h, 10 h, 11 h, 12 h, 13 h, 14 h, 15 h, 16 h, 17 h, 18 h, 19 h, or 20 h; preferably, the fed-batch addition is performed for a time period of 6-12 h. During the fed-batch addition, the degree of supersaturation of the sugar liquid is controlled at between 1.01 and 1.19, preferably between 1.01 and 1.10, and more preferably between 1.03 and 1.08.

In step (2), the sugar liquid is preferably evaporated until sugar degree reaches 55-60% Brix, e.g., 56%, 57%, 58%, or 59% Brix, and more preferably, 58-60% Brix. After the fed-batch addition is completed, concentration is continued for 1-2 h. Preferably, it is 10-15 h, e.g., about 14 h, from the time the seed crystal is added to the time of discharging.

In other embodiments, the preparation method uses scheme 2, which comprises the following steps:

(1) adding water and L-arabinose starting material, stirring while adding the L-arabinose starting material, and adding activated carbon for adsorption after the starting material is completely dissolved by heat; and (2) filtering to remove the activated carbon and adding the resulting material to a reactor for concentration, adding a proper amount of the L-arabinose starting material as seed crystal when the material is concentrated to sugar degree of 55-65% Brix, and cooling the mixture at a rate of 0.5-2° C. per hour.

According to an embodiment of the present disclosure, the seed crystal adopted in the scheme 2 is the same as that adopted in the scheme 1.

According to an embodiment of the present disclosure, in step (1) of the scheme 2, the starting material and the water are in a ratio by mass of 1:(0.5-3), preferably 1:(1-1.5), e.g., 1:(1-1.2); the starting material and the activated carbon are in a ratio by mass of 1:(0.0005-0.01), e.g., 1:0.0005; the activated carbon is allowed to perform adsorption at a temperature of 55-70° C. for a time period of 20-60 min.

In step (2), the sugar liquid is preferably concentrated until sugar degree reaches 58-60% Brix; preferably, the cooling is performed at a rate of 0.5-1.5° C. per hour, e.g., at 1° C. per hour. In a third aspect, the present disclosure also provides an L-arabinose prepared using the preparation method.

In a fourth aspect, the present disclosure also provides a preparation comprising the L-arabinose. The preparation may be in unit dosage form or in multi-dose form. In some embodiments, the preparation is in unit dosage form and comprises 1-100 g of the L-arabinose, preferably 20-60 g of the L-arabinose, e.g., 20 g, 30 g, 40 g, 50 g, or 60 g of the L-arabinose. According to an embodiment of the present disclosure, the preparation is administered at a dose of 20-75 g per day when applied for bowel preparation.

According to an embodiment of the present disclosure, the preparation is an aqueous solution of the L-arabinose; in the aqueous solution, the concentration of the L-arabinose is 0.1-0.6 g/mL (the amount of the L-arabinose in grams per milliliter of water), preferably 0.2-0.5 g/mL, e.g., 0.2, 0.3, 0.4 g/mL.

In a fifth aspect, the present disclosure provides L-arabinose granules. According to an embodiment of the present disclosure, the L-arabinose granules comprise the L-arabinose described above in the first aspect, or the L-arabinose obtained according to the preparation process described above in the third aspect.

In a sixth aspect, the present disclosure provides a preparation method for the L-arabinose granules, which comprises the following steps:

(1) dissolving L-arabinose starting material in water, adding activated carbon, filtering, and removing the activated carbon to give a clear filtered sugar liquid; and (2) subjecting 40-55% (v %) of the clear filtered sugar liquid obtained in step (1) to evaporation until sugar degree reaches 55-65% Brix, adding the remaining clear filtered sugar liquid in a fed-batch manner after adding a proper amount of the L-arabinose starting material as seed crystal, and continuing concentration after the fed-batch addition is completed.

According to an embodiment of the present disclosure, the L-arabinose starting material as the seed crystal is of 40-200 mesh, e.g., 40 mesh, 60 mesh, 80 mesh, or 100 mesh, preferably 80-100 mesh. It can be understood by those skilled in the art that the seed crystal can be obtained by grinding and sieving L-arabinose starting material, for example, with conventional industrial sieves (40-200 mesh) or pharmacopeia standard sieves (No. 3, No. 4, No. 5, No. 6, No. 7, No. 8 and No. 9); for example, with No. 5 and No. 6 pharmacopeia standard sieves. In some embodiments, L-arabinose starting material is ground and sieved with No. 5 and No. 6 pharmacopeia standard sieves, and the part that can pass through the No. 5 sieve but not through the No. 6 sieve is used as the seed crystal. According to an embodiment of the present disclosure, the seed crystal is added in an amount that is e.g., 0.05%, 0.1%, 0.2%, 0.3%, 0.4%, 0.5%, 0.6%, 0.7%, 0.8%, 0.9% or 1%, by mass of the added L-arabinose starting material.

According to an embodiment of the present disclosure, in step (1) of the method, the starting material and the water are in a ratio by mass of 1:(0.5-3), preferably 1:(1-1.5), e.g., 1:1.1 or 1:1.2; the starting material and the activated carbon are in a ratio by mass of 1:(0.0005-0.01), preferably, 1:(0.0005-0.0015), e.g., 1:0.0005 or 1:0.001. Preferably, the activated carbon can be removed by suction filtration under vacuum through microporous filter membranes, or by filtration through a plate and frame filter or a flat-plate microfiltration membrane. 25 μm and 0.45 μm microporous filter membranes can be successively used. Preferably, the activated carbon is added at 50-70° C. After the activated carbon is added, stirring may be performed at 50-70° C. for 20-40 min, e.g., for 30 min.

In step (2), the sugar liquid is preferably evaporated until sugar degree reaches 55-60% Brix, e.g., 56%, 57%, 58% or 59% Brix. After the fed-batch addition is completed, concentration is continued for 1-2 h. Preferably, the evaporation is performed at a temperature of 55-70° C., more preferably, 58-65° C., e.g., 60° C., 61° C., 62° C., 63° C., 64° C. or 65° C. Preferably, it is 10-15 h, e.g., about 14 h, from the time the seed crystal is added to the time of discharging. Preferably, the evaporation is performed with stirring at a rate of 90-110 rpm. In some embodiments, the stirring mode may be selected from double-layered stirring (two-half-crescent type for the lower layer, three-bladed propeller type for the upper layer) and single-layered, 3-to 6-bladed propeller type assisted by forced circulation. Preferably, the fed-batch addition is performed for a time period of 6-24 h, e.g., 9 h, 10 h, 11 h, 12 h, 13 h, 14 h, 15 h, 16 h, 17 h, 18 h, 19 h or 20 h. In some preferred embodiments, the fed-batch addition is performed for a time period of 8-15 h; during the fed-batch addition, the degree of supersaturation of the sugar liquid is controlled at between 1.01 and 1.19, preferably between 1.01 and 1.10, and more preferably between 1.03 and 1.08.

According to an embodiment of the present disclosure, it can be understood by those skilled in the art that the evaporation can be performed under reduced pressure.

According to an embodiment of the present disclosure, the method further comprises the following steps:

(3) continuing the evaporation until sugar cake concentration reaches 75-85% after the fed-batch addition is completed, discharging and centrifuging; and (4) drying to give granules.

According to an embodiment of the present disclosure, in step (3), the evaporation is performed for a time period of 1-3 h, e.g., 2 h; preferably, the evaporation is performed until sugar cake concentration reaches 75-80%, e.g., 75%, 76%, 77%, 78%, 79% or 80%.

In some embodiments, the drying may be selected from one or more of fluidizing drying, fluidized bed drying, and reduced-pressure drying.

In some embodiments, step (4) is specifically:

(4i) fluidizing drying followed by fluidized bed drying to give granules. Preferably, a wind temperature of 90-105° C. and a material temperature of 60-80° C. are adopted for the fluidizing drying. In the fluidized bed drying, stepwise cooling is performed; preferably, 40-50° C. wind is introduced, low-temperature (e.g., 15-25° C.) cold dry wind is delivered, and finally, the temperature is lowered to room temperature.

According to an embodiment of the present disclosure, in step (4i), back-mixing bed fluidizing drying may be used; during the drying, a star unloader or rotary feeder may be used for feeding; preferably, the feeding is assisted by vibration.

In some embodiments, step (4) is specifically: manually spreading material, and drying in a drying oven under reduced pressure and vacuum.

According to an embodiment of the present disclosure, the method further comprises step (5): packaging. Preferably, during the packaging, a vibration unloading mode is adopted, and quantification is performed by linear weighing.

According to an embodiment of the present disclosure, the method optionally comprises the following steps: further sieving the dried particles.

According to an embodiment of the present disclosure, the arabinose is β-L-(+)-arabinose. In some embodiments, the L-arabinose granules comprise the L-arabinose described above in the first aspect, or the L-arabinose obtained according to the preparation process described above in the third aspect. In a seventh aspect, the present disclosure also provides L-arabinose granules prepared using the preparation method.

According to an embodiment of the present disclosure, the L-arabinose particles have an average particle size ranging from 100 μm to 600 μm, preferably from 100 μm to 300 μm, e.g., 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm or 290 μm. The L-arabinose particles have a D10 of 40-200 μm, preferably, 40-100 μm, e.g., 40 μm, 50 μm, 60 μm, 70 μm, 80 μm, 90 μm or 100 μm. The L-arabinose particles have a D50 of 80-200 μm, preferably, 90-150 μm, e.g., 90 μm, 100 μm, 110 μm, 120 μm, 130 μm, 140 μm or 150 μm. The L-arabinose particles have a D90 of 150-300 μm, preferably, 200-250 μm, e.g., 200 μm, 210 μm, 220 μm, 230 μm, 240 μm or 250 μm. According to an embodiment of the present disclosure, the granules may be in unit dosage form or in multi-dose form. In some embodiments, the granules are in unit dosage form and comprise 1-100 g of L-arabinose, e.g. 1 g, 5 g, 10 g, 20 g, 30 g, 40 g, 50 g or 60 g of L-arabinose. In some embodiments, the granules are administered at a dose of 20-75 g per day; in other embodiments, the granules are administered at a dose of 3-20 g per day.

In an eighth aspect, the present disclosure also provides a method for using the L-arabinose and preparations described above (including the L-arabinose and preparations thereof referred to in the first, third, fourth, fifth and seventh aspects) for bowel cleansing and/or bowel preparation.

According to an embodiment of the present disclosure, in bowel cleansing and/or bowel preparation, g, e.g., 20 g, 30 g, 40 g, 50 g or 60 g, of the L-arabinose and preparation can be administered each time; to complete one bowel cleansing and/or bowel preparation, the L-arabinose and preparation are administered at a total dose of 20-75 g. In some embodiments, the present disclosure provides a method for using the L-arabinose granules for bowel cleansing and/or bowel preparation, body weight control and the amelioration and/or treatment of constipation. When the granules are used for bowel cleansing and/or bowel preparation, 20-60 g, e.g., 20 g, 30 g, 40 g, 50 g or 60 g, of the L-arabinose granules can be administered each time. In some embodiments, to complete one bowel cleansing and/or bowel preparation, the L-arabinose granules are administered at a total dose of 20-75 g; in other embodiments, when the granules are used for body weight control and the amelioration and/or treatment of constipation, 3-20 g of the L-arabinose granules is administered daily.

In a ninth aspect, the present disclosure also provides use of the L-arabinose and preparations (including the L-arabinose and preparations thereof referred to in the first, third, fourth, fifth and seventh aspects) for the manufacturing of medicaments for bowel cleansing and/or bowel preparation. In some embodiments, the present disclosure provides use of the L-arabinose granules for the manufacturing of medicaments for bowel cleansing and/or bowel preparation, body weight control and the amelioration and/or treatment of constipation.

Beneficial Effects

1) After monocrystal growing, the L-arabinose product prepared by the present disclosure is identified as a single β-crystalline form. The L-arabinose product prepared by the present disclosure can be directly applied as a bowel cleanser drug without adding other auxiliary agents. It has good flowability, and is safe and effective. It greatly improves the textures and tastes of drugs for bowel preparation and increases the administrable dosage range, significantly increases patient compliance, and reduces most patients' psychological resistance to conventional drugs for bowel preparation. It is superior to magnesium sulfate and PEG conventionally recommended in clinical practice in all aspects, and also has certain advantages over sorbitol hypertonic liquid.

2) The preparation process adopted by the present disclosure is simple and easy to implement, and the crystallization process does not involve use of organic solvents. The preparation process is environment-friendly and safe, and with it, the range of particle size of the product is easy to control. The purity of the obtained product can reach 99.6% or higher, and single impurities are all controlled to be within the limit range of 0.05%. The product is up to the standard of starting material drugs for high-quality bowel preparation. Particularly, the process of the present disclosure controls the fructose content at 0 and the galactose content at 0.01-0.04% in the product, so the unnecessary effects and burdens caused by the absorption of fructose and galactose on patients can be reduced or avoided. It is especially suitable for people with fructose intolerance to take the product safely. 3) In the process of preparing arabinose granules, the present disclosure does not involve addition of any auxiliary material nor complicated granulation processes. The obtained product has good flowability in the packaging and filling processes and has proper granularity distribution, capable of meeting the requirements of the existing pharmacopoeia on granularity and quality.

DETAILED DESCRIPTION

Figure 1:
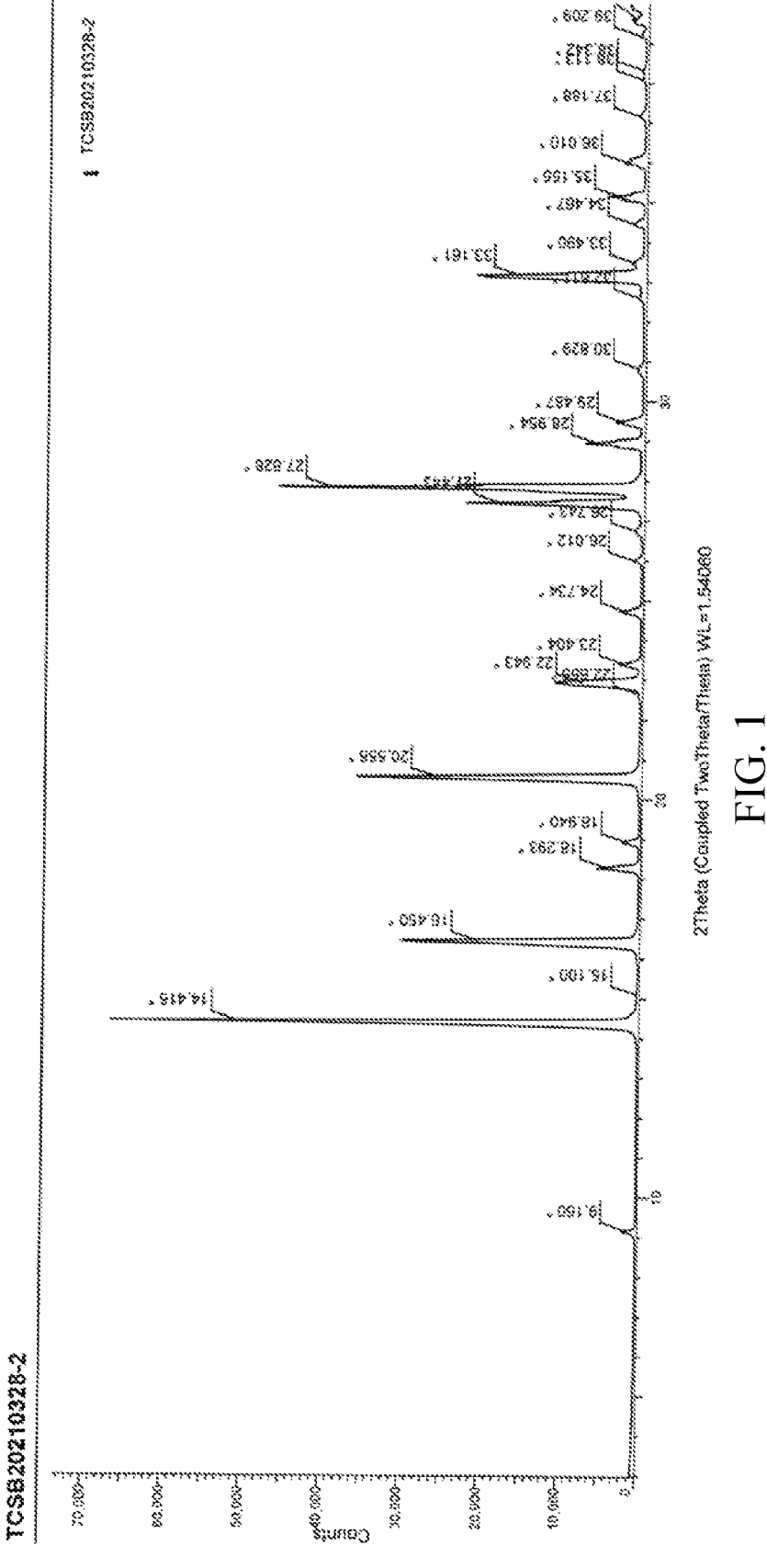
FIG. 1 shows a powder X-ray diffraction pattern of the L-arabinose according to the present disclosure.
Figure 2:
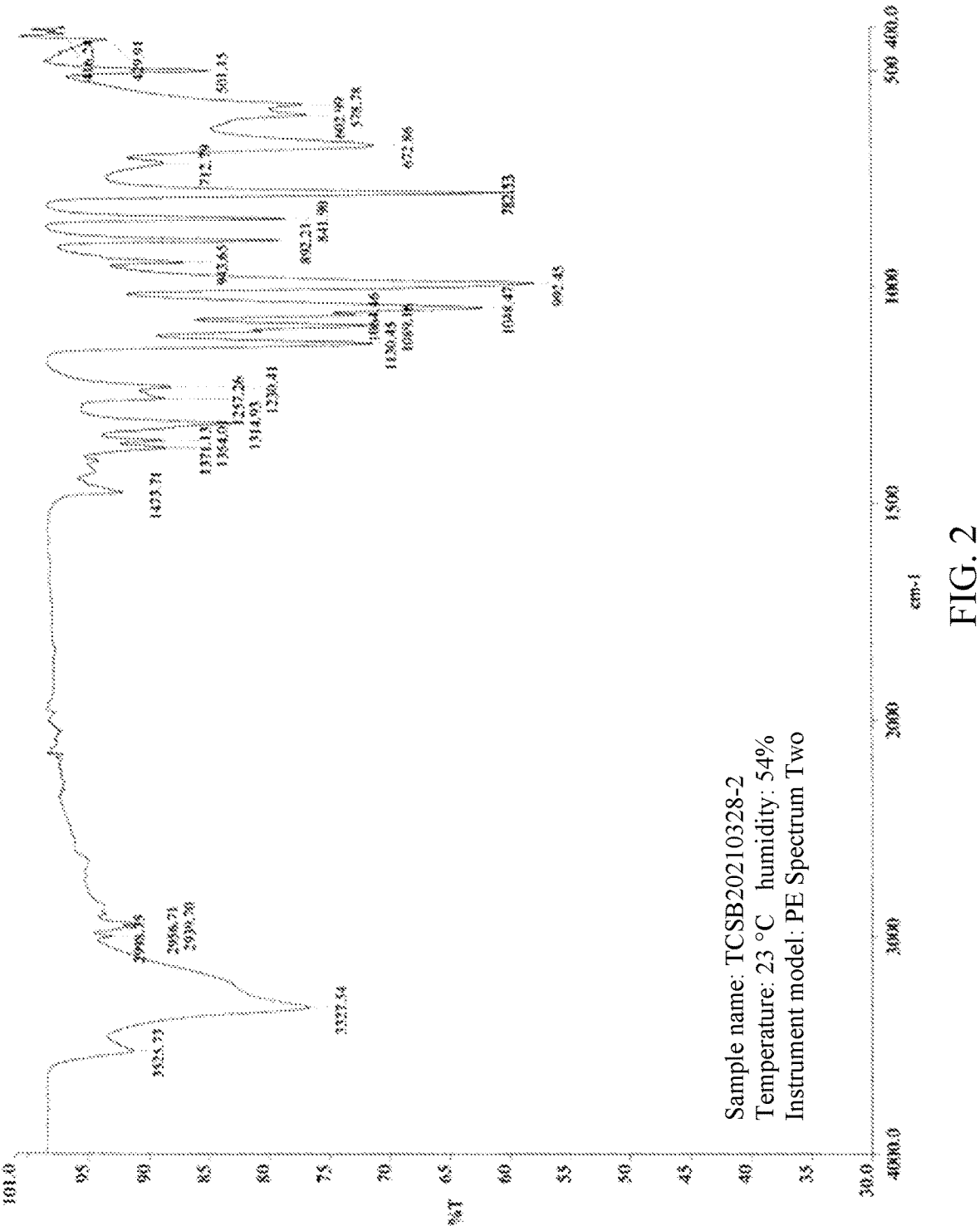
FIG. 2 shows an infrared spectrum of the L-arabinose according to the present disclosure.
Figure 3:
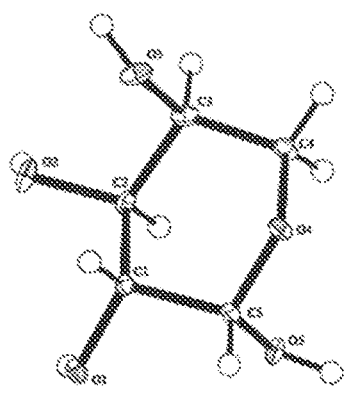
FIG. 3 illustrates the monocrystal diffraction structure of L-arabinose.

The technical scheme of the present disclosure will be further illustrated in detail with reference to the following specific examples. It should be understood that the following embodiments are merely exemplary illustration and explanation of the present disclosure, and should not be construed as limiting the protection scope of the present disclosure. All techniques implemented based on the content of the present disclosure described above are encompassed within the protection scope of the present disclosure.

Unless otherwise stated, the starting materials and reagents used in the following examples are all commercially available products or can be prepared using known methods.

The L-arabinose starting material used in the following examples was purchased from Thomson Biotech (Xiamen) Pte., Ltd. and has ≥99% purity (which meets the national standards of L-arabinose QB/T 4321-2012).

Example 1. Preparation of L-Arabinose by Evaporative Fed-Batch Crystallization 30 kg of L-arabinose starting material was weighed out and dissolved in 33 kg of purified water at ° C. 30 g of activated carbon was added. The mixture was incubated at 60° C. for 40-60 min, and filtered to remove the activated carbon to give a clear filtered sugar liquid.

About half of the clear filtered sugar liquid was added to an evaporative crystallization tank and evaporated until the sugar degree reached 58-60% Brix. After a proper amount of the L-arabinose starting material was added as seed crystal (the seed crystal was a powder obtained by grinding and sieving the L-arabinose starting material (with No. 5 and No. 6 pharmacopeia standard sieves), the part that could pass the No. 5 sieve but not the No. 6 sieve), the remaining half of the clear filtered sugar liquid was added in a fed-batch manner at a rate of 1.5-4.0 L/h for a time period of 10-12 h. After the fed-batch addition was completed, the concentrating was continued for 1-2 h. It was about 14 h from the time the seed crystal was added to the time of discharging.

It can be understood by those skilled in the art that the term "fed-batch addition" is one of the conventional operations of evaporative crystallization—that is, continuously replenishing the sugar liquid while evaporating water to keep the liquid concentration of the sugar liquid in the system relatively constant. For example, during the fed-batch addition described above, the degree of supersaturation of the sugar liquid did not exceed 1.10.

| Category | Liquid phase purity (%) | Galactose % | Fructose % | Product yield % |
|---|---|---|---|---|
| Arabinose starting material | 99.07 | 0.115 | 0.06 | — |
| Product of Example 1 (first batch) | 99.68 | 0.03 | 0 | 47 |
| Product of Example 1 (second batch) | 99.71 | 0.04 | 0 | 48.7 |

The X-ray powder diffraction of the crystal of the L-arabinose using Cu-Kα radiation and represented by 2θ angles was carried out using the test instrument D8 advance (Bruker) X-ray diffractometer with the following instrument parameters:

Radiation: Cu K ($\lambda$=1.54056);
Working current: 40 mA;
Working voltage: 40 KV;
Detector: PSD;
Start angle: 4° (2-theta);
Stop angle 40° (2-theta);
Scanning step: 0.05°/step;
Scanning speed: 1 sec/step.

The results of the measurement are shown in FIG. 1. The error range for 2θ angles is ±0.20°. The L-arabinose prepared in Example 1 was 149 μm in average particle size and had the particle size distribution as follows: D10=49 D50=138 D90=261 μm and span=0.985, as determined by particle size analysis.

After monocrystal growing, the L-arabinose product prepared in Example 1 was identified as β-L-(+)-arabinose by a monocrystal diffractometer. In the specific implementation process, the L-arabinose monocrystal was grown using the interface diffusion method: 20 g of the prepared L-arabinose was dissolved in 20 mL of deionized water; after it was completely dissolved, the solution was cooled to room temperature, and then 40 mL of ethanol was added via the inner wall of the beaker; the beaker was sealed with plastic wrap to prevent ethanol evaporation; shaking of solution was avoided as much as possible during ethanol addition and sealing. The beaker was placed in a constant-temperature water bath set at 30° C. After about 1 month, an L-arabinose monocrystal was obtained. The crystal is an orthorhombic crystal system with a space group of $P2_12_12_1$, and the unit cell parameters are as follows:

a=4.78120(10)Å,
b=6.43740(10)Å,
c=19.50095(3)Å,
a=90°, β=90°, γ=90°, V=600.208(18)Å$^3$, Z=4, F(000) =320.0.

Example 2. Preparation of L-Arabinose by Cooling Crystallization

Sugar dissolution: 25 L of water and 22 kg of L-arabinose starting material were added to a sugar-dissolving tank. Stirring was performed as the L-arabinose was added. After the L-arabinose was completely dissolved by heat, 22 g of activated carbon was added. Adsorption was performed for 20-60 min by incubating the mixture at 55-70° C. After the activated carbon was removed by filtration, the material was added to a reactor and concentrated. When the sugar degree reached 60% Brix, a proper amount of the L-arabinose starting material was added as seed crystal (the seed crystal was a powder obtained by grinding and sieving the L-arabinose starting material (with No. 5 and No. 6 pharmacopeia standard sieves), the part that could pass the No. 5 sieve but not the No. 6 sieve). The seed crystal was added at a temperature of 60° C. The rate of stirring was adjusted to 50 rpm. A cooling program was executed. The initial cooling temperature was 60° C., and the rate of cooling was 1° C./h. The results of liquid chromatography measurement are shown in the table below (% purity was calculated by area normalization, i.e., the ratio of the component to be measured to the total peak area of the sample):

| Category | Liquid phase purity (%) | Period of crystallization | Galactose % | Fructose % | Finished product yield % |
|---|---|---|---|---|---|
| L-Arabinose starting material | 99.1 | | 0.095 | 0.05 | — |
| Product of Example 2 | 99.68 | 36 h | 0.03 | 0 | 43.1 |
| Product of Example 3 | 99.63 | 16 h | 0.04 | 0 | 40.8 |

The product of Example 2 was found to be free of D-arabinose (an article (Higaki S, et al., *Journal of the Food Hygienic Society of Japan*, 2018, 59(3):114-120) describes that D-arabinose is toxic and that there is a safety risk from eating it) and furfural.

The L-arabinose product prepared in Example 2 was identified to have the same crystalline form as the product prepared in Example 1, and was 189 μm in average particle size and had the particle size distribution as follows: D10=82 μm, D50=182 μm and D90=299 μm, as determined by particle size analysis.

Example 3

Example 3 is substantially the same as Example 2 in terms of operation except that the rate of cooling was increased to about 2° C./h, and that the period of crystallization was shortened to 16 h, close to that of the evaporative fed-batch crystallization. The finished product yield of crystallization was 40.8%. The average particle size was 125 μm, and the particle size distribution was as follows: D10=43 μm, D50=109 μm and D90=232 μm, as determined by particle size analysis.

Example 4. Particle Size Parameters and Powder Characteristics (Quantity Distribution) of L-Arabinose

TABLE 4-1

Particle size parameter test results (BT-2900 image particle size analysis system)

| Product | Example 1 | Example 2 | Example 3 | Commercial product (T1) | Commercial product (Y1) |
|---|---|---|---|---|---|
| Average particle size (μm) | 149 | 189 | 125 | 75 | 33 |
| D10 (μm) | 49 | 82 | 43 | 27 | 11 |

TABLE 4-1-continued

| | Particle size parameter test results (BT-2900 image particle size analysis system) | | | | |
| --- | --- | --- | --- | --- | --- |
| Product | Example 1 | Example 2 | Example 3 | Commercial product (T1) | Commercial product (Y1) |
| D50 (μm) | 138 | 182 | 109 | 63 | 30 |
| D90 (μm) | 261 | 299 | 232 | 137 | 63 |

TABLE 4-2

| | Flowability test results (particle and powder characteristic analyzer, FT-102D) | | | | |
| --- | --- | --- | --- | --- | --- |
| Product | Example 1 | Example 2 | Example 3 | Commercial product (T1) | Commercial product (Y1) |
| Flowability (angle of repose) | Relatively good | Relatively good | Relatively good | Relatively poor | Relatively poor |
| Flowability (Hausner ratio) | Good | Good | Good | Very poor | Very poor |
| Hausner ratio | 1.2 | 1.3 | 1.2 | 1.7 | 1.7 |
| Compressibility | 17.1 | 20.6 | 24.3 | 40.2 | 41.4 |
| Carr flowability index | 100.5 | 102.5 | 99 | 79 | 79 |
| Floodability index | 75.0 | 75.0 | 75.0 | 75 | 75 |
| Angle of repose | 40.01 | 38.95 | 38.76 | 51.05 | 51.73 |
| Tap density | 0.85 | 0.76 | 0.74 | 0.93 | 0.85 |
| Bulk density | 0.7 | 0.6 | 0.56 | 0.55 | 0.50 |

Example 5. Using the L-Arabinose Prepared by the Present Disclosure for Bowel Preparation in Mice 5.1 Experimental animals and feeding thereof: SPF (Specific pathogen free) mice, 6 weeks old; normal feed was D12450-B feed: 67.35 wt % carbohydrates, 19.2 wt % crude protein, 4.3 wt % fat. The temperature of the room was kept at 24-26° C. with humidity at 40-60%.

5.2 Experimental method and procedure:

The SPF mice were randomly divided into a blank control group, a positive control group and a treatment group, 20 mice per group, half being male and half female. The dosage administered to each group is shown in Table 1 below. Administration method: Animals in each group were fasted (water was accessible) from last 22:00 before the day of experiment, were each given ⅓ the calculated amount of drug by intragastrical administration at 7:00, 9:00 and 11:00 on the day of experiment, were each given 0.1 mL of purified water at 12:00, 13:00 and 14:00, and were dissected 3.5 h after the last administration.

TABLE 5-1

| Group | Treatment | Administration dosage (g/kg) | Administration volume (mL/kg) |
| --- | --- | --- | --- |
| Negative control group | Purified water | / | 42 |
| Positive control group | PEG | 31.5 | 42 |

TABLE 5-1-continued

| Group | Treatment | Administration dosage (g/kg) | Administration volume (mL/kg) |
| --- | --- | --- | --- |
| Treatment group | L-Arabinose prepared in Example 1 | 12 | 30 |

Note:
The test substance was administered to each administration group in three doses.

Results:

(1) Watery and loose stools were observed in both the positive control group and the treatment group before the dissection.

(2) It was observed that no residue was left in the rectum and colon in the positive control group and the treatment group after the dissection, which indicates good bowel cleansing effects. Apparently, it took only a dosage that was 38% of that administered to the positive control group for the L-arabinose treatment group to achieve the same effect. The treatment group has a significant advantage in terms of administration dosage.

Example 6. Using the L-Arabinose Prepared by the Present Disclosure for Bowel Preparation in Humans Administration Sample: L-Arabinose Prepared in Example 1

Subject: male, 41 years old, weighing 73 kg
Administration Regimen:

The subject drank water normally on an empty stomach after getting up in the morning.

At 10:06, the subject dissolved 30 g of L-arabinose in about 100-150 mL of mineral water and consumed the solution in about 5 min.

About 40 min later, at 10:42, the subject drank about 350 mL of water, and then went to the bathroom and passed loose stool.

Twenty-five minutes later, at 11:11, the subject drank another 100 mL of water, and then went to the bathroom for the second time and passed watery stool.

After about another 15 min, at 11:34, the subject drank another 250 mL of water.

At 11:55, the subject went to the bathroom for the third time and passed watery stool with little residue.

At 12:10, the subject drank 200 mL of water.

At 13:27, the subject went to the bathroom for the fourth time and passed light yellow watery stool without residue.

In the whole process, about 1 L of water was consumed. The whole process took 3 and a half hours. Therefore, the L-arabinose product prepared by the present disclosure can be directly taken with water. It is convenient to take. The dosage is modest. It can effectively meet the requirements for bowel cleansing and preparation before operation, enteroscopy or other examinations.

Example 7. In Vitro Osmotic Pressure Test for the L-Arabinose Prepared by the Present Disclosure Instrument: Vapro Pressure Osmometer
Materials: L-Arabinose (Prepared According to the Method of Example 1); Sorbitol (Commercially Available Chinese Medicinal Agent)

Procedure: The 4 numbered solutions were each prepared according to the material proportions shown in Table 2 and stirred until they were all clear and transparent. Then they were each assayed, and the results are shown in Table 7-1 below.

TABLE 7-1

Comparison of sorbitol hypertonic liquid and L-arabinose solution in terms of osmotic pressure

| No. | Material proportion Sorbitol g | L-Arabinose g | Purified water g | Osmotic pressure A mmol/kg | Osmotic pressure B mmol/kg | Average osmotic pressure mmol/kg | Percent increase in osmotic pressure % | Mass concentration % |
|---|---|---|---|---|---|---|---|---|
| 1 | 15 | 0 | 35 | 2385 | 2405 | 2395 | | 30 |
| 2 | 0 | 15 | 35 | 2941 | 2940 | 2940 | 22.8% | 30 |
| 3 | 0.75 | 14.25 | 35 | 2953 | 2920 | 2936 | 22.6% | 30 |
| 4 | 3.0 | 12 | 35 | 2839 | 2881 | 2860 | 19.4% | 30 |

Note:
Osmotic pressure A and osmotic pressure B represent the results of parallel tests for identically numbered samples. The average osmotic pressure refers to the average of osmotic pressure A and osmotic pressure B.

As can be seen from the table above, at the same mass concentration, the L-arabinose has 22.8% higher osmotic pressure than sorbitol hypertonic liquid, which indicates that a solution of the L-arabinose solution of the present disclosure can strengthen the osmotic pressure in bowels based on the osmotic pressure effect of the solution itself after being orally taken, having a certain advantage over sorbitol hypertonic liquid.

Example 8. Preparation of L-Arabinose Particles

1.1. Procedure 1 kg of L-arabinose starting material was dissolved in 1.2 kg of purified water at 60° C. After the solution was completely clear, 1 g of activated carbon (1% by mass of the L-arabinose) was added. The mixture was incubated at 60° C. for 30 min and then subjected to suction filtration under vacuum successively through 25 μm and 0.45 μm filter membranes to remove the activated carbon, and a clear filtered sugar liquid (about 1800 mL in volume) was obtained. About 800 mL of the clear filtered sugar liquid was It can be understood by those skilled in the art that the term "fed-batch addition" is one of the conventional operations of evaporative crystallization—that is, continuously replenishing the sugar liquid while evaporating water to keep the liquid concentration of the sugar liquid in the system relatively constant. During the fed-batch addition described above, the degree of supersaturation of the sugar liquid was controlled within a range of 1.01-1.10.

According to the results shown in Table 8-1, the specific surface area of the seed crystal of 80-100 mesh is relatively small compared with that of the seed crystal of other specifications (as shown in Table 8-2), but the particle size distribution of the sample obtained by experiment is relatively uniform: the proportion of 20-80 mesh is more than 89.7%, and the maximum proportion is more than 90%, which fully complies with the requirements of the existing pharmacopoeia (Chinese pharmacopoeia (2020)) for granules: granules cannot pass through a No. 1 sieve (10 mesh, 2000 μm) and the total quantity of granules which can pass through a No. 5 sieve (80 mesh, pore size of 180 nm) should not exceed 15%.

TABLE 8-1

Effects of seed crystal's specification on sample' granularity distribution (standard sieve)

| No. | Specification of seed crystal | Weight of seed crystal g | Proportion in feed amount % | Time h | Granularity distribution of sample (standard sieve) >20 mesh | 20-80 mesh | <80 mesh |
|---|---|---|---|---|---|---|---|
| 1 | 40-60 mesh | 16.5 | 1.65 | 18 | 23.4 | 71.2 | 5.4 |
| 2 | 60-80 mesh | 6 | 0.8 | 18 | 38 | 61 | 1 |
| 3 | 80-100 mesh | 1.5 | 0.15 | 18 | 16.9 | 81.6 | 1.5 |
| 4 | 80-100 mesh | 1.5 | 0.15 | 12 | 5.3 | 90.5 | 4.2 |
| 5 | 80-100 mesh | 1.5 | 0.15 | 12 | 7.3 | 89.7 | 3 | added to a three-necked flask, and stirred and evaporated under reduced pressure in a water bath set at a temperature of 62° C. until the sugar degree reached 58-60% Brix. A proper amount of L-arabinose was added as seed crystals (as shown in Table 8-1 below, seed crystal with different specifications was selected: 40-60 mesh, 16.5 g; 60-80 mesh, 6 g; 80-100 mesh, 1.5 g). The mixture was stirred (double-layered type of stirring, with two-half-crescent type for the lower layer and three-bladed propeller type for the upper layer) at a rate of 90-110 rpm until the seed crystal was completely dispersed. Then the sugar liquid was added at a rate of 50-100 mL/h in a fed-batch manner for a time period of 12/18 h. After the fed-batch addition was completed, the concentrating was continued for 1-2 h. It was about 14 h from the time the seed crystal was added to the time of discharging.

TABLE 8-2

Parameters of seed crystal

| Mesh number range of seed crystal | Specific surface area m²/g | Number of particles g | Weight of added seed crystal g | Total number of particles | Total specific surface area m² |
|---|---|---|---|---|---|
| 40-60 | 0.018 | 6000 | 16.5 | 99000 | 0.297 |
| 60-80 | 0.024 | 18000 | 6 | 108000 | 0.144 |
| 80-100 | 0.033 | 65000 | 1.5 | 97500 | 0.0495 |

Note:
The specific surface area and the number of particles of seed crystal were determined using a dynamic image particle size analysis system.

15 16

Example 9. Monocrystal Growing and Identification of L-Arabinose

The L-arabinose product prepared in Example 8 was used and identified as β-L-(+)-arabinose by a monocrystal diffractometer after monocrystal growing. The L-arabinose monocrystal was grown using the interface diffusion method: 40 g of the prepared L-arabinose was dissolved in 40 mL of deionized water; after it was completely dissolved, the solution was cooled to room temperature, and then 80 mL of ethanol was added via the inner wall of the beaker; the beaker was sealed with plastic wrap to prevent ethanol evaporation; shaking of the solution was avoided as much as possible during ethanol addition and sealing. The beaker was placed in a constant-temperature water bath set at 30° C. After about 15 days, an L-arabinose monocrystal was obtained. The crystal is an orthorhombic crystal system with a space group of $P2_12_12_1$.

TABLE 9-1

Dimensions of monocrystals (it took 15 × 24 = 360 h to grow them)

| Crystal No. | Length mm | Width mm |
| --- | --- | --- |
| 1 | 4.2 | 1.5 |
| 2 | 8.8 | 2.1 |
| 3 | 5.5 | 1.8 |
| 4 | 7.3 | 2.7 |
| 5 | 6.1 | 1.2 |
| 6 | 6.3 | 1.3 |
| 7 | 4.0 | 2.0 |
| 8 | 6.0 | 2.0 |
| 9 | 7.8 | 2.5 |
| 10 | 8.5 | 2.3 |
| Range | 4000 um-8800 um | 1200 um-2700 um |

Note:
Ten pieces of crystal were randomly picked out of the grown monocrystal. The actual length was slightly greater than these values as some crystal pieces broke when picked up.

Example 10. Preparation of L-Arabinose Granules

After 8000 kg of L-arabinose starting material was completely dissolved in 8800 kg of purified water by stirring and heat, 4 kg of activated carbon was added to the solution at 60° C. The mixture was incubated with stirring for 30 min and then filtered to remove the activated carbon to give a clear purified liquid. About 8400 kg (about 7200 L) of the clear purified liquid was added to an evaporative crystallization vessel and evaporated at a sugar liquid temperature of 60-65° C. The sugar liquid was concentrated by the evaporation to 59.4% Brix. Seed crystal of 80-100 mesh was added at a temperature of 64.9° C. The remaining other half of the clear filtered liquid was added at a rate of about 600 L/h in a fed-batch manner for 12 h. Evaporative crystallization was performed under reduced pressure. After the fed-batch addition was completed, the evaporation was continued for about 2 h. Discharging and centrifugation were performed when the sugar cake concentration was 81%. Fluidizing drying was performed using a screw continuous feeding back-mixing bed (wind temperature of 90-105° C., material temperature of 60-80° C.). Then fluidized bed drying and stepwise cooling were performed (40-50° C. wind was introduced, and low-temperature (15-25° C.) cold dry wind was delivered). After the temperature was lowered to room temperature, packaging was performed.

It can be understood by those skilled in the art that "sugar cake" refers to a solid-liquid mixture of arabinose crystal and sugar liquid, and that "sugar cake concentration" refers to the concentration of arabinose in the solid-liquid mixture.

TABLE 10-1

Preparation process parameters

| Batch No. | Mesh number/weight of seed crystal | Fed-batch addition time | 20-80 mesh proportion of sample[a] % | 20-80 mesh proportion of sample[b] % |
| --- | --- | --- | --- | --- |
| Batch 1 | 80-100 mesh/12 kg | 12 h | 66.4 | 93.0 |
| Batch 2 | 80-100 mesh/9 kg | 12 h | 79.8 | 96.4 |

Note:
The superscript [a] indicates that the sample was obtain by adopting a screw feeding-back-mixing bed drying manner during drying.
The superscript [b] indicates that the sample was obtained by adopting a post-centrifugation sampling-manual material spreading and drying oven drying manner.

Example 11. Preparation of L-Arabinose Granules

After 30 kg of L-arabinose starting material was completely dissolved in 33 kg of purified water by stirring and heat, 15.2 g of activated carbon was added to the solution at 60° C. The mixture was incubated with stirring for 30 min and then filtered to remove the activated carbon to give a clear purified liquid. About 32 kg of the clear purified liquid was added to a reactor and evaporated under reduced pressure at a sugar liquid temperature of 60-65° C. The sugar liquid was concentrated by the evaporation to 57.6% Brix. 45 g of seed crystal of 80-100 mesh was added at a temperature of 61.5° C. The remaining other half of the clear filtered liquid was added at a rate of 2-2.3 L/h in a fed-batch manner for 12 h. After the fed-batch addition was completed, the evaporation was continued for about 2 h. Discharging and centrifuging were performed when the sugar cake concentration was 78%. The material was spread manually and dried using a drying oven.

Example 12. Preparation of L-Arabinose Granules

After 40 kg of L-arabinose starting material was completely dissolved in 44 kg of purified water by stirring and heat, 20.2 g of activated carbon was added to the solution at 60° C. The mixture was incubated with stirring for 30 min and then filtered to remove the activated carbon to give a clear purified liquid. About 32 kg of the clear purified liquid was added to a reactor and evaporated under reduced pressure at a sugar liquid temperature of 60-65° C. The sugar liquid was concentrated by the evaporation to 57.6% Brix. 60 g of seed crystal of 80-100 mesh was added at a temperature of 61.5° C. The remaining other half of the clear filtered liquid was added at a rate of 2-2.3 L/h in a fed-batch manner for 12 h. After the fed-batch addition was completed, the evaporation was continued for about 2 h. Discharging and centrifuging were performed when the sugar cake concentration was 78%. The material was spread manually and dried using a drying oven (dried under reduced pressure and vacuum).

TABLE 12-1

Preparation process parameters

| Product | Mesh number/ weight of seed crystal | Fed-batch addition time | 20-80 mesh proportion of sample % |
| --- | --- | --- | --- |
| Example 11 | 80-100 mesh/45 g | 12 h | 90.6 |
| Example 12 | 80-100 mesh/60 g | 12 h | 93.57 |

Note:
The manual material spreading and drying oven drying manner was adopted in these examples.

Example 13. Performance Test Results for the Granules of the Present Disclosure

TABLE 13-1

Flowability test results (particle and powder characteristic analyzer, FT-102D)

| Product | Example 10 batch 1 | Example 10 batch 2 | Example 11 | Example 12 |
|---|---|---|---|---|
| Flowability (angle of repose) | Rela-tively good | Rela-tively good | Rela-tively good | Rela-tively good |
| Flowability (Hausner ratio) | Good | Good | Acceptable | Good |
| Hausner ratio | 1.2 | 1.2 | 1.3 | 1.3 |
| Compressibility | 17.1 | 15.9 | 23.1 | 24.4 |
| Carr flowability index | 100.5 | 102.5 | 102.0 | 99 |
| Floodability index | 75.0 | 75.0 | 75.0 | 75.0 |
| Angle of repose | 40.01 | 30.95 | 34.29 | 39.74 |
| Tap density | 0.85 | 0.81 | 0.65 | 0.64 |
| Bulk density | 0.7 | 0.68 | 0.5 | 0.48 |

Note:
Two batches of sample of Example 10 for flowability tests were both obtained by adopting a screw feeding-back-mixing bed drying manner.

TABLE 13-2

Granularity distribution (quantity distribution) of finished products (BT-2900 image particle size analysis system)

| Product | Example 10 sample of batch 1[a] | Example 10 Sample of batch 1[b] | Example 10 sample of batch 2[a] | Example 10 Sample of batch 2[b] | Example 11 | Example 12 |
|---|---|---|---|---|---|---|
| Average particle size (μm) | 134.5 | 182 | 129.2 | 189 | 148.8 | 185.5 |
| D10 (μm) | 48.4 | 78 | 41.88 | 79 | 164.8 | 175.1 |
| D50 (μm) | 125.1 | 174 | 116.4 | 168 | 288.1 | 305.2 |
| D90 (μm) | 230.6 | 296 | 237.9 | 331 | 448.8 | 481.8 |

Note:
The superscript [a] indicates that the sample was obtain by adopting a screw feeding-back-mixing bed drying manner.
The superscript [b] indicates that the sample was obtained by adopting a post-centrifugation sampling-manual material spreading and drying oven drying manner.

Example 14

The procedure was the same as that in the process of Example 10 except that the feeding was performed using a star unloader. Accordingly, the material spreading height of back-mixing bed fluidizing drying was reduced by a factor of 3 or greater—that is, the material spreading thickness was less than 16 cm (the original height was about 50 cm).

TABLE 14-1

| Product | Mesh number/weight of seed crystal | Fed-batch addition time | 20-80 mesh proportion of sample[a] % | 20-80 mesh proportion of sample[c] % |
|---|---|---|---|---|
| Example 14 | 80-100 mesh/15 kg | 12 h | 94.3% | 89% |

Note:
The superscript [a] indicates that the sample was obtain by adopting a post-centrifugation sampling-manual material spreading and drying oven drying manner.
The superscript [c] indicates that the sample was obtained by star valve unloading-back-mixing bed drying.

Example 15. Saturation Curve and Crystallization Curve of L-Arabinose

Figure 4:
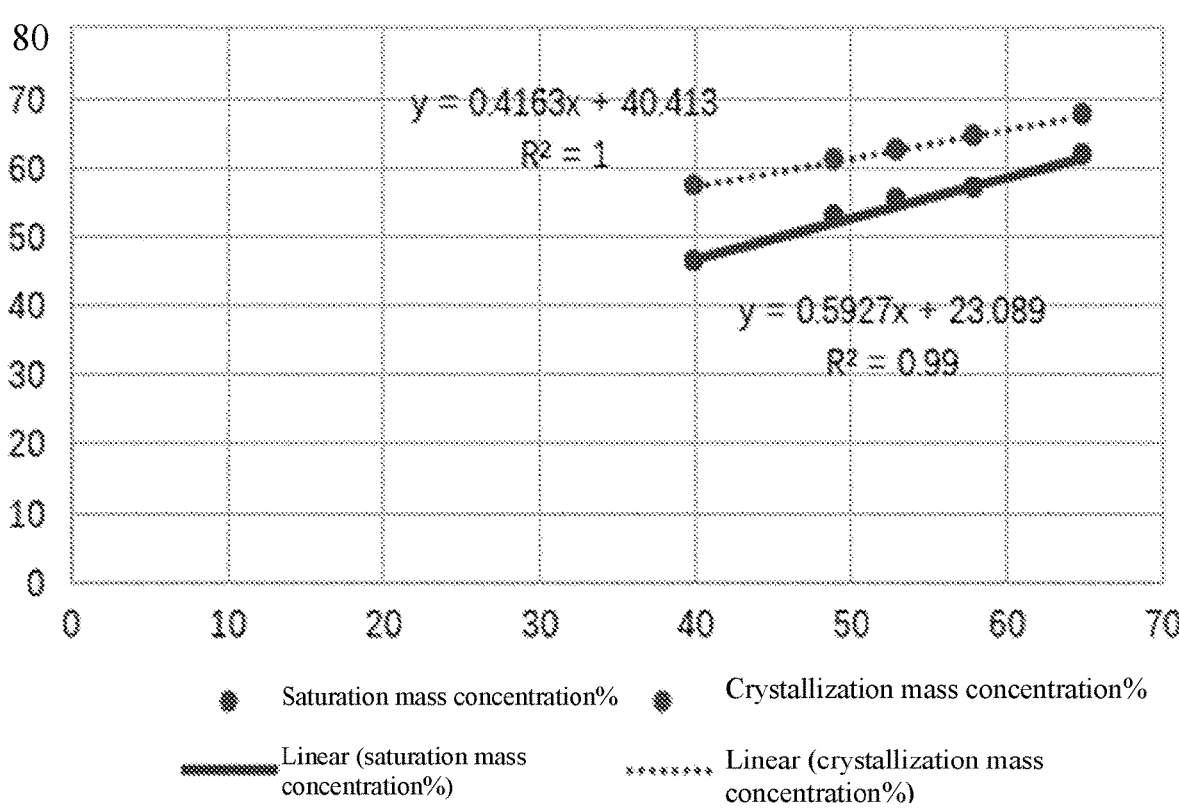
FIG. 4 illustrates a saturation curve and a crystallization curve of arabinose.

A round-bottom flask was plated in a constant-temperature box with temperature control. To a three-necked round-bottom flask (one flask mouth was plugged with a plastic stopper as a sampling mouth, one flask mouth was used for placing a stirrer, and one flask mouth was used for temperature sensing) were added a certain amount of ionized water and excessive L-arabinose crystal (prepared according to the method of Example 10). The mixture was stirred at 40° C., 49° C., 53° C., 58° C. and 65° C. for 3 h per temperature point, and then let stand for 4 h to allow the undissolved L-arabinose crystal to completely settle. Then the supernatant was collected and filtered through a microporous filter membrane (for filtration using a small injection needle in the constant-temperature box to eliminate the effect of temperature change). The resulting clear liquid was used for concentration determination. A saturation curve was plotted for arabinose: $y=0.5927x+23.089$ (correlation coefficient $R^2=0.99$) (see FIG. 4). Clear sugar liquids in which corresponding mass concentrations of L-arabinose were dissolved was prepared, then slowly cooled (1° C./h), and cooled at a constant rate (with stirring at 100 rpm). The crystallization temperature of the sugar liquids with different mass concentrations was observed and recorded. A crystallization curve was plotted for arabinose: $y=0.4163x+40.413$ (correlation coefficient $R^2=1$) (see FIG. 4 and Table 15-1). As can be seen from Table 15-1, if the crystallization temperature is 65° C., the concentration of the sugar liquid exceeds 67.47% (the degree of supersaturation exceeds 1.1) during fed-batch addition at this time, and then a large amount of powdered crystal will appear, and the number of crystals dramatically increases, which prevents the crystals from growing to a greater size—that is, the crystallization fails; the system needs to be dissolved by heat and recrystallized.

TABLE 15-1

Saturation curve and crystallization curve data of arabinose

| Temper-ature ° C. | Saturation mass concentration % | Crystallization mass concentration % | Supersaturation coefficient |
|---|---|---|---|
| 40 | 46.3 | 57.07 | 1.233 |
| 49 | 52.7 | 60.81 | 1.154 |
| 53 | 55.1 | 62.48 | 1.134 |
| 58 | 56.9 | 64.56 | 1.135 |
| 65 | 61.5 | 67.47 | 1.097 |

Example 16. Packaging of L-Arabinose Granules

The L-arabinose finished product prepared in Example 14 was packaged at a rate of 15-40 packs/min in a single channel. Airtightness and deliverable volume examinations were performed during the packaging so it met the production requirements. In the packaging process of the packaging machine, a vibration unloading mode was adopted, and the quantity was determined by linear weighing. The obtained L-arabinose granules met the requirements of the pharmacopoeia (2020 edition) for the granularity and deliverable volume of granules.

Equipment model: MK-600

TABLE 16-1

| Name | Parameters and requirements |
| --- | --- |
| Packing material | Arabinose finished product prepared according to Example 14 |
| Weight of package | 1-30 g |
| Edge-sealing form | Three-edge sealing |
| Dimensions of package | Determining width and length according to deliverable volume |
| Rate of packaging | 15-40 packs/min |
| Mode of measuring | 1. Precise linear weighing<br>2. Vibration unloading |
| Packaging accuracy | ±6% for deliverable volume not greater than 6 g, ±4% for deliverable volume greater than 6 g. |
| Dimensions of mold | Ruled |
| Mode of cutting | Horizontal cutting |
| Photoelectric sensor | Provided |
| Easy-to-tear cut | Provided |

Note:
The packaging specification selected for this equipment model was 1-30 g. The packaging specifications were: 5 g, preparation pack's dimensions: 65 mm x 85 mm; 20 g, preparation pack's dimensions: 65 mm x 130 mm. A deliverable volume of 31-100 g can be achieved by only replacing the equipment's pack maker and former according to the preparation pack's dimensions.

The embodiments of the present disclosure have been described above. However, the present disclosure is not limited to the embodiments described above. Any modification, equivalent, improvement and the like made without departing from the spirit and principle of the present disclosure shall fall within the protection scope of the present disclosure.

The invention claimed is:

1. A method for preparing L-arabinose granules, comprising:

(1) dissolving L-arabinose starting material in water, adding activated carbon, filtering, and removing the activated carbon to give a clear filtered sugar liquid; and (2) subjecting 40-55% (v %) of the clear filtered sugar liquid obtained in step (1) to evaporation until sugar degree reaches 55-65% Brix, adding the remaining clear filtered sugar liquid in a fed-batch manner after adding a proper amount of the L-arabinose starting material as seed crystal, and continuing concentration after the fed-batch addition is completed, wherein:

the L-arabinose starting material used as the crystal seed is of 80-100 mesh;

the seed crystal is added in an amount that is 0.05-1% by mass of the added L-arabinose starting material;

in step (1), the starting material and the water are in a ratio by mass of 1:(0.5-3);

in step (2), the sugar liquid is evaporated until sugar degree reaches 55-60% Brix;

the L-arabinose granulates has an average particle size ranging from 100 μm to 600 μm, and each comprises ≤0.04% galactose and ≤0.05% fructose by mass;

the L-arabinose is β-L-(+)-arabinose;

the L-arabinose granulates contain one or more β-L-(+)-arabinose crystals of an orthorhombic crystal system, each crystal having a $P2_12_12_1$ space group and unit cell parameters of:

a=4.78120(10) Å, b=6.43740(10) Å, c=19.50095(3) Å, $\alpha$=90°, $\beta$=90°, $\gamma$=90°, V=600.208(18) Å$^3$, Z=4, and F (000)=320.0;

during the fed-batch addition, the degree of supersaturation of the sugar liquid is controlled at between 1.01 and 1.19;

and the L-arabinose starting material has an L-arabinose purity greater than 99% calculated by area normalization.

2. The preparation method as claimed in claim 1, wherein the evaporation is performed at a temperature of 55-70° C.; the fed-batch addition is performed for a time period of 6-24 h.

3. The preparation method as claimed in claim 1, further comprising the following steps:

(3) continuing the evaporation until sugar cake concentration reaches 75-85% after the fed-batch addition is completed, discharging and centrifuging; and (4) drying to give granules.

4. The preparation method as claimed in claim 3, wherein the drying is selected from one or more of fluidizing drying, fluidized bed drying, and reduced-pressure drying.

5. The preparation method as claimed in claim 3, wherein during the drying, a star unloader or rotary feeder is used for feeding.

6. The preparation method as claimed in claim 1, wherein a crystal of the L-arabinose granule has X-ray powder diffraction peaks measured using Cu-Kα radiation at 2θ angles of 14.416±0.20°, 16.450±0.20°, 20.556±0.20°, 27.443±0.20°, 27.828±0.20° and 33.161±0.20°.

7. The preparation method as claimed in claim 1, wherein a crystal of the L-arabinose granule has X-ray powder diffraction peaks measured using Cu-Kα radiation at 2θ angles of 14.416±0.20°, 16.450±0.20°, 20.556±0.20°, 22.943±0.20°, 27.443±0.20°, 27.828±0.20° and 33.161±0.20°.

8. The preparation method as claimed in claim 1, wherein a crystal of the L-arabinose granule has an X-ray powder diffraction pattern as shown in FIG. 1.

* * * * *